(12) United States Patent
Shrivastava et al.

(10) Patent No.: US 11,087,879 B2
(45) Date of Patent: Aug. 10, 2021

(54) SYSTEM AND METHOD FOR PREDICTING HEALTH CONDITION OF A PATIENT

(71) Applicant: Conduent Business Services, LLC, Dallas, TX (US)

(72) Inventors: Harsh Shrivastava, Bangalore (IN); Vijay Huddar, Bijapur (IN); Sakyajit Bhattacharya, Bangalore (IN); Vaibhav Rajan, Bangalore (IN)

(73) Assignee: Conduent Business Services, LLC, Florham Park, NJ (US)

( * ) Notice: Subject to any disclaimer, the term of this patent is extended or adjusted under 35 U.S.C. 154(b) by 597 days.

(21) Appl. No.: 15/242,667

(22) Filed: Aug. 22, 2016

(65) Prior Publication Data
US 2018/0052961 A1   Feb. 22, 2018

(51) Int. Cl.
*G16H 50/20* (2018.01)
*G16H 40/63* (2018.01)
(Continued)

(52) U.S. Cl.
CPC ............ *G16H 50/20* (2018.01); *G06F 16/00* (2019.01); *G06F 16/285* (2019.01); *G06F 16/35* (2019.01);
(Continued)

(58) Field of Classification Search
CPC ........ G16H 50/20; G16H 10/60; G16H 40/63; G06F 16/285; G06F 16/35; G06F 16/00;
(Continued)

(56) References Cited

U.S. PATENT DOCUMENTS

| 8,015,136 B1 * | 9/2011 | Baker ................ G16H 50/30 706/45 |
| 2006/0074821 A1 * | 4/2006 | Cristianini .......... G06K 9/6215 706/12 |

(Continued)

FOREIGN PATENT DOCUMENTS

WO   WO-2014201515 A1 * 12/2014 ............. G16H 50/30

OTHER PUBLICATIONS

Barbara Engelhardt, Kernels and Kernel Methods, Oct. 9, 2013 (Year: 2013).*
(Continued)

*Primary Examiner* — Elaine Gort
*Assistant Examiner* — Amanda R. Covington
(74) *Attorney, Agent, or Firm* — Jones Robb, PLLC

(57) ABSTRACT

According to embodiments illustrated herein, there is provided a system for predicting a health condition of a patient. The system further includes one or more processors configured to separately cluster data points from a set of medical records associated with a first class of patients and a second class of patients. A similarity value of each of the clustered data points with respect to a pre-selected subset of data points that represents landmark points may be determined, using a parameterized similarity measure. One or more classifiers are trained using the determined similarity value of each data point. The trained one or more classifiers are adapted to learn one or more parameters of the parameterized similarity measure during the training. An occurrence of the health condition of the patient may be predicted based on the trained one or more classifiers and one or more medical records of the patient.

20 Claims, 6 Drawing Sheets

(51) Int. Cl.

| | |
|---|---|
| G16H 10/60 | (2018.01) |
| G06F 16/28 | (2019.01) |
| G06F 16/00 | (2019.01) |
| G06F 16/35 | (2019.01) |
| G06N 20/00 | (2019.01) |
| G06N 20/10 | (2019.01) |

(52) U.S. Cl.
CPC ............ *G06N 20/00* (2019.01); *G06N 20/10* (2019.01); *G16H 10/60* (2018.01); *G16H 40/63* (2018.01)

(58) Field of Classification Search
CPC .......... G06F 19/00; G06F 19/30; G06F 19/32; G06F 19/34; G06Q 50/22; G06Q 50/24
USPC ........................................................ 705/2, 3
See application file for complete search history.

(56) References Cited

U.S. PATENT DOCUMENTS

| | | | | |
|---|---|---|---|---|
| 2007/0149862 | A1* | 6/2007 | Pipke | A61B 5/0205 600/301 |
| 2010/0063948 | A1* | 3/2010 | Virkar | G06N 20/00 706/12 |
| 2011/0082712 | A1* | 4/2011 | Eberhardt, III | G06Q 10/10 705/4 |
| 2013/0236567 | A1* | 9/2013 | Martin | G06Q 50/22 424/649 |
| 2014/0089003 | A1* | 3/2014 | Frey | G06Q 10/06 705/3 |
| 2014/0378810 | A1* | 12/2014 | Davis | A61B 5/7278 600/407 |
| 2015/0324527 | A1* | 11/2015 | Siegel | G16H 10/60 705/3 |
| 2017/0124263 | A1* | 5/2017 | Crafts, Jr. | G16H 40/20 |
| 2017/0124279 | A1* | 5/2017 | Rothman | G16H 10/60 |
| 2017/0140114 | A1* | 5/2017 | Are | G06N 20/00 |
| 2017/0286623 | A1* | 10/2017 | Tekumalla | G16H 50/30 |
| 2018/0011972 | A1* | 1/2018 | Rajan | G16H 50/30 |

OTHER PUBLICATIONS

Kan Deng, Omega: On-line Memory-Based General Purpose System Classifier, Nov. 1998, Canegie Mellon University (Year: 1998).*

Maria-Florina Balcan, Avrim Blum, and Nathan Srebro. A theory of learning with similarity functions. Machine Learning, 72(1-2):89-112, 2008.

Siong Thye Goh and Cynthia Rudin. Box drawings for learning with imbalanced data. In Proc. 20th ACM SIGKDD international conference on Knowledge discovery and data mining, pp. 333-342. ACM, 2014.

Ronaldo C Prati, Gustavo EAPA Batista, and Maria Carolina Monard. Class imbalances versus class overlapping: an analysis of a learning system behavior. In MICAI 2004: Advances in Artificial Intelligence, pp. 312-321. Springer, 2004.

Thore Graepel, Ralf Herbrich, Bernhard Scholkopf, Alex Smola, Peter Bartlett, K-R Muller, Klaus Obermayer, and Robert Williamson. Classification on proximity data with LP-machines. In Proc. International Conference on Artificial Neural Networks, pp. 304-309, 1999.

K. Veropoulos, C. Campbell, and N. Cristianini. Controlling the sensitivity of support vector machines. In Proceedings of the International Joint Conference on AI, pp. 55-60, 1999.

C.X. Ling and V.S. Sheng. Cost-sensitive learning and the class imbalance problem. In Sammut C (Ed) Encyclopedia of machine learning. Springer, 2008.

P. Kang and S. Cho. EUS SVMs: Ensemble of under-sampled SVMs for data imbalance problems. In Neural Information Processing Systems (NIPS), Lecture Notes in Computer Science, vol. 4232, pp. 837-846. 2006.

Hongyu Guo and Herna L. Viktor. Learning from imbalanced data sets with boosting and data generation: the DataBoost-IM approach. Bibliometrics, 6(1):30-39, 2004.

Mohammed Saeed, C Lieu, G Raber, and RG Mark. MIMIC II: a massive temporal ICU patient database to support research in intelligent patient monitoring. In Computers in Cardiology, 2002, pp. 641-644, 2002.

Robert Johnson, Ahsan Arozullah, Neumayer Leigh, William G. Henderson, Patrick Hosokawa, and Shukri F. Khuri. Multivariable predictors of postoperative respiratory failure after general and vascular surgery: Results from the patient safety in surgery study. Journal of the American College of Surgeons, 204(6):1188-1198, 2007.

Foster Provost and Tom Fawcett. Robust classification for imprecise environments. Machine learning, 42(3):203-231, 2001.

Yihua Chen, Eric K. Garcia, Maya R. Gupta, Ali rahimi, and Luca Cazzanti. Similarity-based classification: Concepts and Algorithms. The Journal of Machine Learning Research, 10:747-776, 2009.

Purushottam Kar and Prateek Jain. Similarity-based learning via data driven embeddings. In Advances in neural information processing systems, pp. 1998-2006, 2011.

* cited by examiner

SYSTEM AND METHOD FOR PREDICTING HEALTH CONDITION OF A PATIENT

TECHNICAL FIELD

The presently disclosed embodiments are related, in general, to healthcare systems. More particularly, the presently disclosed embodiments are related to a system and a method for predicting health condition of a patient.

BACKGROUND

The healthcare industry covers tasks such as the management and maintenance of various records, ranging from birth certificates to death certificates. Generally, a patient's health condition may be predicted based on datasets received from various heterogeneous electronic sources, such as discharge summaries. Such datasets are prepared at different time periods during the course of treatment. For example, discharge summaries are usually available only at the time of discharge of the patient. Therefore, such datasets may not be useful in predicting the health condition of the patient while the patient is under medical observation (for instance, when the patient is in an intensive care unit (ICU)).

Further, most datasets in healthcare are imbalanced—containing significantly more samples from one class (the majority class) than the other class (the minority class, e.g., patients diagnosed with the health condition). For such imbalanced datasets, standard classifiers may attempt to reduce the overall misclassification error, which may bias the classifiers towards majority class in the imbalanced datasets. Thus, such classifiers may not be able to identify test samples from the minority class efficiently. Consequently, the health condition of a new patient may not be predicted accurately using the imbalanced dataset as reference. Thus, an advanced learning technique may be desired for classifying imbalanced data so that health condition of a new patient under medical observation may be predicted accurately by using the imbalanced dataset.

SUMMARY

According to embodiments illustrated herein, there is provided a system for predicting a health condition of a patient by use of a computing device. The system includes one or more transceivers in the computing device configured to retrieve a set of medical records of a plurality of patients from a memory device, wherein the set of medical records corresponds to a first class of patients diagnosed with the health condition and a second class of patients not diagnosed with the health condition. The system includes one or more processors in the computing device configured to separately cluster data points associated with the first class of patients and the second class of patients. The one or more processors are further configured to determine a similarity value of each of the clustered data points with respect to a pre-selected subset of data points that represents landmark points, using a parameterized similarity measure. The one or more processors are further configured to train one or more classifiers using the determined similarity value of each data point, wherein the one or more classifiers are adapted to learn one or more parameters of the parameterized similarity measure during the training. The one or more processors are further configured to predict an occurrence of the health condition of the patient based on the trained one or more classifiers and one or more medical records of the patient. The one or more processors are further configured to render the predicted occurrence of the health condition of the patient on a display, via a user interface.

According to embodiments illustrated herein, there is provided a method for predicting a health condition of a patient using a computing device. The method includes retrieving, by one or more transceivers in the computing device, a set of medical records of a plurality of patients from a memory device, wherein the set of medical records corresponds to a first class of patients diagnosed with the health condition and a second class of patients not diagnosed with the health condition. The method includes separately clustering, by one or more processors in the computing device, data points associated with a first class of patients and a second class of patients. The method further includes determining, by the one or more processors, a similarity value of each of the clustered data points with respect to a pre-selected subset of data points that represents landmark points, using a parameterized similarity measure. The method further includes training, by the one or more processors, one or more classifiers using the determined similarity value of each data point, wherein the one or more classifiers are adapted to learn one or more parameters of the parameterized similarity measure during the training. The method further includes predicting, by the one or more processors, an occurrence of the health condition of the patient based on the trained one or more classifiers and one or more medical records of the patient. The method further includes rendering, by the one or more processors, the predicted occurrence of the health condition of the patient on a display, via a user interface.

According to embodiments illustrated herein, there is provided a computer program product for use with a computer. The computer program product includes a non-transitory computer readable medium. The non-transitory computer readable medium stores a computer program code for predicting a health condition of a patient using a computing device. The computer program code is executable by one or more processors to retrieve, by use of one or more transceivers in the computing device, a set of medical records of a plurality of patients from a memory device. The set of medical records corresponds to a first class of patients diagnosed with the health condition and a second class of patients not diagnosed with the health condition. The computer program code is further executable by the one or more processors to separately cluster data points associated with the first class of patients and the second class of patients. The computer program code is further executable by the one or more processors to determine a similarity value of each of the clustered data points with respect to a pre-selected subset of data points that represents landmark points, using a parameterized similarity measure. The computer program code is further executable by the one or more processors to train one or more classifiers using the determined similarity value of each data point, wherein the one or more classifiers are adapted to learn one or more parameters of the parameterized similarity measure during the training. The computer program code is further executable by the one or more processors to predict an occurrence of the health condition of the patient based on the trained one or more classifiers and one or more medical records of the patient. Additionally, the computer program code is further executable by the one or more processors to render the predicted occurrence of the health condition of the patient on a display, via a user interface.

BRIEF DESCRIPTION OF DRAWINGS

The accompanying drawings illustrate various embodiments of systems, methods, and other aspects of the disclosure. Any person having ordinary skill in the art will appreciate that the illustrated element boundaries (e.g., boxes, groups of boxes, or other shapes) in the figures represent one example of the boundaries. It may be that in some examples, one element may be designed as multiple elements, or that multiple elements may be designed as one element. In some examples, an element shown as an internal component of one element may be implemented as an external component in another, and vice versa. Furthermore, elements may not be drawn to scale.

Various embodiments will hereinafter be described in accordance with the appended drawings, which are provided to illustrate, and not to limit the scope in any manner, wherein like designations denote similar elements, and in which.

DETAILED DESCRIPTION

Figure 1:
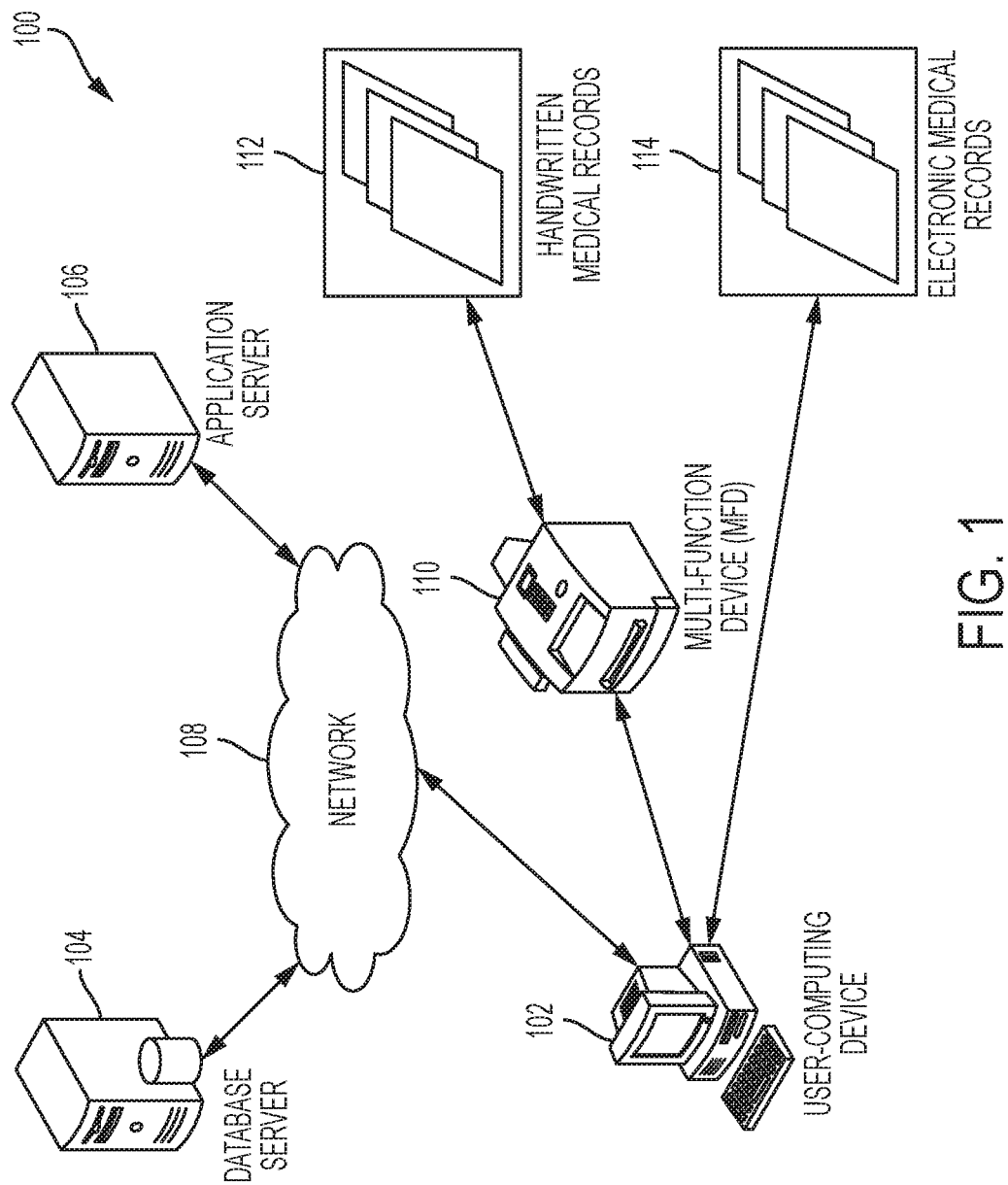
FIG. 1 is a block diagram that illustrates a system environment in which various embodiments may be implemented, in accordance with at least one embodiment.

The present disclosure is best understood with reference to the detailed figures and description set forth herein. Various embodiments are discussed below with reference to the figures. However, those skilled in the art will readily appreciate that the detailed descriptions given herein with respect to the figures are simply for explanatory purposes as the methods and systems may extend beyond the described embodiments. For example, the teachings presented and the needs of a particular application may yield multiple alternate and suitable approaches to implement the functionality of any detail described herein. Therefore, any approach may extend beyond the particular implementation choices in the following embodiments described and shown.

References to "one embodiment," "an embodiment," "at least one embodiment," "one example," "an example," "for example," and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in an embodiment" does not necessarily refer to the same embodiment.

Definitions

The following terms shall have, for the purposes of this application, the respective meanings set forth below.

A "computing device" refers to a device that includes one or more processors/microcontrollers and/or any other electronic components, or a device or a system, which performs one or more operations according to one or more programming instructions/codes. Examples of a computing device may include, but are not limited to, a desktop computer, a laptop, a personal digital assistant (PDA), a mobile device, a smartphone, a server, and/or a tablet computer.

A "Multi-function Device (MFD)" refers to a device that can perform multiple functions. Examples of the functions may include, but are not limited to, printing, scanning, copying, faxing, emailing, and the like. In an embodiment, the MFD includes a scanner and a printer for scanning and printing one or more documents (i.e., medical records, such as nursing notes, investigative reports, and other medical notes written by healthcare professionals) respectively. In an embodiment, the MFD has communication capabilities that enable it to send/receive data and messages, in accordance with one or more communication protocols, such as, but not limited to, FTP, WebDAV, E-Mail, SMB, NFS, and TWAIN.

A "patient" is a human being who may require medical care or treatment by a medical expert, such as a doctor. In another words, a patient is any recipient of health care services. In an embodiment, the patient may refer to a human being who is currently under medical observation. In an embodiment, a plurality of patients may refer to multiple patients who were under medical observation in the past.

A "medical record" refers to the documentation of health condition of a patient. The medical record may include notes, such as nursing notes or progress notes, documented over time by a healthcare professional (a doctor, a nurse, a medical attender, etc.). In an embodiment, medical records may include recorded observations, administered drugs, and therapies, test results, x-rays, nursing reports, investigative reports, etc. In an embodiment, the medical record may be documented on a computing device such as, but not limited to, a desktop computer, a laptop, a PDA, a mobile device, a smartphone, a tablet computer, and the like. In an embodiment, the medical record may be an electronic or handwritten document. In case of the handwritten document (such as on a paper), the medical record may be scanned to obtained the electronic form.

A "nursing note" refers to a medical record that may describe a health condition of a patient and a treatment given or planned. The nursing note may be documented by a nurse, physician, and other healthcare professionals that usually focus on documenting the health condition of the patient. The nursing notes that describe a patient's condition may be periodically recorded (approximately once 3 to 4 hours) by attending clinical staff in ICU. The nursing note may comprise, but is not limited to, prescribed treatments, response to the prescribed treatments, or diagnosis. The nursing note corresponding to the patient is recorded daily in the hospital. Hereinafter, "nursing note" and "nursing report" may be interchangeably used.

An "investigative report" refers to a medical report that may be representative of the state and progress of a patient. In an embodiment, the investigative report may comprise, but is not limited to, one or more reports from radiology, microbiology, and biochemistry. In an embodiment, the investigative reports may be periodically recorded during a patient's stay in a hospital. Hereinafter, "investigative note" and "investigative report" may be interchangeably used.

A "medical specialty" refers to a branch of medical science that specializes in a treatment of a particular type of ailment or a body part. Examples of medical specialties include, but are not limited to, cardiology, rheumatology, nephrology, neurology, endocrinology, hematology, dermatology, ophthalmology, and so on.

A "user" refers to a medical professional such as, but not limited to, a doctor, a nurse, a medical attendant, a hospital staff, or any other healthcare professional. In an embodiment, the user may be an individual who may not as such belong to a medical profession but may operate the computing device of the disclosure.

A "sensor" refers to a device that detects/measures events or changes in quantities and provides a corresponding output, generally as an electrical or optical signal. In medical science, the sensor may be operable to detect biological, physical, and/or chemical signals associated with a first patient and may measure and record those signals. For example, pressure sensors, temperature sensors, and humidity sensors are used to monitor and regulate gas flow and gas conditions in anesthesia machines, respirators, and ventilators.

FIG. 1 is a block diagram that illustrates a system environment 100 in which various embodiments may be implemented. The system environment 100 includes a user-computing device 102, a database server 104, an application server 106, and a network 108. There is further shown a MFD 110, handwritten medical records 112, and electronic medical records 114. Various devices in the system environment 100 may be interconnected over the network 108. FIG. 1 shows, for simplicity, one user-computing device 102, one database server 104, and one application server 106. However, it will be apparent to a person having ordinary skill in the art that the disclosed embodiments may also be implemented using multiple user-computing devices, multiple database servers, and multiple applications servers.

The user-computing device 102 refers to a computing device used by a user. The user-computing device 102 may comprise one or more processors. The user-computing device 102 may be configured to execute one or more sets of instructions stored in one or more memory devices. In an embodiment, the user-computing device 102 may be communicatively coupled to the network 108. In an embodiment, the user-computing device 102 may comprise a display screen that may be configured to display one or more user interfaces to a user. In an embodiment, the user may utilize the user-computing device 102 to transmit or receive data pertaining to a patient to/from the database server 104 and/or the application server 106 over the network 108. For example, the user may transmit, using the user-computing device 102, one or more medical records of the patient. For example, the user may transmit a nursing note or an investigative note. The one or more medical records may be handwritten medical records 112 or electronic medical records 114.

In an embodiment, the user-computing device 102 may receive the electronic medical records 114 from one or more medical departments, such as a nursing department, a radiology department, and/or a laboratory department. In another embodiment, the user-computing device 102 may be coupled to an MFD 110. Though, the MFD 110 is implemented outside the user-computing device 102 in FIG. 1, a person skilled in the art will appreciate that the MFD 110 may be implemented as a part of the user-computing device 102 without departing from the scope of the disclosure. Further, in an embodiment, the MFD 110 may scan the one or more medical records, such as the handwritten medical records 112, to generate the corresponding electronic medical records, which may be transmitted to the user-computing device 102. In an embodiment, the user may utilize the user-computing device 102 to provide one or more inputs to perform one or more operations such as, but not limited to, scanning of a medical record (e.g., handwritten nursing note on a paper) and retrieving a set of medical records from a memory device. The memory device may be an in-built memory, such as the one or more memory devices, of the user-computing device 102, or an external device, such as the database server 104. The user-computing device 102 may correspond to various types of computing devices such as, but not limited to, a desktop computer, a laptop, a personal digital assistant (PDA), a mobile device, a smartphone, a tablet computer, and the like.

The database server 104 may refer to a computing device that may store healthcare or clinical data, such as a set of medical records, of a plurality of patients, in accordance with at least one embodiment. The set of medical records may be historical medical records. In an embodiment, the database server 104 may store metadata pertaining to the set of medical records of the plurality of patients. The metadata pertaining to the set of medical records of the plurality of patients may include, but is not limited to, one or more medical complications developed during their stay in hospital, clinical notes (such as nursing notes, investigative reports, medication and allergies reports, laboratory test results, and radiology images), personal statistics (such as age and weight), and other reports, such as measures of vital signs. The set of medical records may correspond to a first class of patients diagnosed with a certain health condition and a second class of patients not diagnosed with the health condition. In an embodiment, the database server 104 may retrieve the set of medical records from various clinical data sources. The clinical data sources may include, but are not limited to, databases of various medical organizations that may provide a rightful authentication to access the information pertaining to the one or more second patients or from publicly available databases, such as Multi-parameter Intelligent Monitoring in Intensive Care (MIMIC II).

In an embodiment, the database server 104 may be communicatively coupled over the network 108. In an embodiment, the database server 104 may be configured to transmit or receive one or more instructions/metadata to/from one or more devices, such as the user-computing device 102 and the application server 106 over the network 108. In an embodiment, the database server 104 may receive a query from the user-computing device 102 or the application server 106 to retrieve the set of medical records of the plurality of patients. For querying the database server 104, one or more querying languages, such as SQL, QUEL, DMX or the like, may be utilized. Further, the database server 104 may be realized through various technologies, which includes, but are not limited to Microsoft® SQL server, Oracle, and My SQL.

The application server 106 may refer to a computing device or a software framework that may provide a generalized approach to create the application server 106 implementation. In an embodiment, the function of the application server 106 may be dedicated to the efficient execution of procedures, such as, programs, routines, or scripts stored in an inbuilt memory device for supporting its applied applications. In an embodiment, the user may access the application server 106 over the network 108 to submit the one or more medical records of the patient (e.g., through the user interface). The one or more medical records of the patient may be nursing notes and/or investigative reports. Further, clinical investigation data, such as laboratory test results, radiology images, allergies reports, and sensor-based patient monitoring data may also be provided to the application server 106. Examples of the sensor-based patient monitoring data include, but are not limited to, data on blood pressure, heart rate, blood sugar level, body temperature, and the like. Alternatively, the application server 106 may retrieve the one or more medical records of the patient from the database server 104. Further, in an embodiment, the application server 106 may transmit a query to retrieve the set of medical records of the plurality of patients from the database server 104 over the network 108.

In an embodiment, the application server 106 may utilize a query, a program, an algorithm, or a code to segregate the set of medical records of the plurality of patients into two classes. The first class of patients, such as "the minority class," may be the patients diagnosed with a particular health condition during their ICU stay. The first class of patients may be the underrepresented class, where the total number of patients may be much lesser compared with those in the second class of patients. The second class of patients, such as "the majority class," may be the patients not diagnosed with the health condition during their ICU stay. The second class of patients may be an overrepresented class. Due to the rarity of the health condition, datasets associated with the first class of patients and the second class of patients may be imbalanced. In an embodiment, the application server 106 may separately cluster data points associated with the first class of patients and the second class of patients. The application server 106 may determine a similarity value of each of the clustered data points with respect to a preselected subset of data points that represents landmark points. The similarity value may be determined by use of a parameterized similarity measure.

In an embodiment, the application server 106 may train one or more classifiers using the determined similarity value of each data point. The one or more classifiers may be adapted to learn one or more parameters of the parameterized similarity measure during the training. Such learning of the one or more parameters of the parameterized similarity measure during the training may improve classification performance for such imbalanced datasets. The one or more classifiers may be implemented using one or more machine learning algorithms (e.g., support vector machine (SVM)). In an embodiment, the application server 106 may predict an occurrence of the health condition of a new patient based on the trained one or more classifiers. The trained one or more classifiers may be applied on one or more medical records of the new patient for such prediction. The application server 106 may be realized using various technologies such as, but not limited to, Java application server, .NET Framework, PHP, and App server. The application server 106 has been described later in conjunction with FIG. 2.

A person skilled in the art will understand that the scope of the disclosure should not be limited to the database server 104 or the application server 106 as a separate entity. In an embodiment, the functionalities of the database server 104 and the application server 106 may be combined into a single server without limiting the scope of the disclosure.

The network 108 corresponds to a medium through which content and messages may flow between various devices, such as the user-computing device 102, the database server 104, and the application server 106. Examples of the network 108 may include, but are not limited to, a Wireless Fidelity (Wi-Fi) network, a Wide Area Network (WAN), a Local Area Network (LAN), or a Metropolitan Area Network (MAN). Various devices such as the user-computing device 102, the database server 104, and the application server 106, may connect to the network 108 in accordance with various wired and wireless communication protocols such as Transmission Control Protocol/Internet Protocol (TCP/IP), User Datagram Protocol (UDP), and 2G, 3G, or 4G Long Term Evolution (LTE) communication protocols.

The MFD 110 refers to a device that can perform multiple functions. Examples of the functions may include, but are not limited to, printing, scanning, copying, faxing, emailing, and the like. In an embodiment, the MFD 110 includes a scanner and a printer for scanning and printing one or more documents (i.e., medical records, such as a nursing note, investigative report, and other medical notes written by healthcare professionals) respectively. In an embodiment, the MFD 110 has communication capabilities that enable the MFD 110 to send/receive data and messages in accordance with one or more communication protocols such as, but not limited to, FTP, WebDAV, E-Mail, SMB, NFS, and TWAIN.

A person skilled in the art will understand that the scope of the disclosure should not be limited to the MFD 110 coupled to the user-computing device 102 as an only entity. In an embodiment, the MFD 110 may be coupled to the database server 104 or the application server 106 without limiting the scope of the disclosure. Further, in an embodiment, the MFD 110 may be depicted inside or outside the database server 104 or the application server 106 without departing from the scope of the disclosure. Further, in an embodiment, the MFD 110 may be connected to the database server 104 or the application server 106 over the network 108 without limiting the scope of the disclosure.

The handwritten medical records 112 may correspond to a handwritten document (such as on a paper) documented by a nurse, physician, and other healthcare professionals. The handwritten medical records 112 may describe a health condition of a patient and a treatment given or planned. The handwritten medical records 112 may be periodically recorded (approximately once every three to four hours) by attending clinical staff in an intensive care unit (ICU). The handwritten medical records 112 may comprise, but are not limited to, prescribed treatments, response to the prescribed treatments, or diagnosis. In an embodiment, the handwritten medical records 112 may be scanned to obtain the electronic form.

The electronic medical records 114 refer to a documentation of health condition of a patient. The electronic medical records 114 may include notes, such as nursing notes or progress notes, documented over time by a healthcare professional (a doctor, a nurse, a medical attender, etc.). In an embodiment, the electronic medical records 114 may include recorded observations, administered drugs, and therapies, test results, x-rays, nursing reports, investigative reports, etc. In an embodiment, the electronic medical records 114 may be documented on a computing device, such as, but not limited to, a desktop computer, a laptop, a PDA, a mobile device, a smartphone, a tablet computer, and the like.

A person having ordinary skill in the art will understand that the scope of the disclosure is not limited to obtaining the electronic form of the one or more medical records by scanning the one or more handwritten medical records, such as the handwritten medical records 112. In an embodiment, the medical records may be documented in an electronic form at the first go (depicted by electronic medical records 114 in FIG. 1). In such a scenario, the medical attender may have a tablet device that allows the medical attender to document notes. The tablet device may have an input means (touch screen of an input pen) that facilitates the medical practitioner to write notes directly on the tablet. In an embodiment, the tablet may include a software that presents a platform to the user of the tablet to write notes. Further, the written notes may be stored in the database server 104.

Further, the notes may be stored in the cloud. Further, the scope of the disclosure is not limited to a tablet device. In an embodiment, any computing device (such as a computer, laptop, phone, and smartphone) may be used for inputting the notes.

Figure 2:
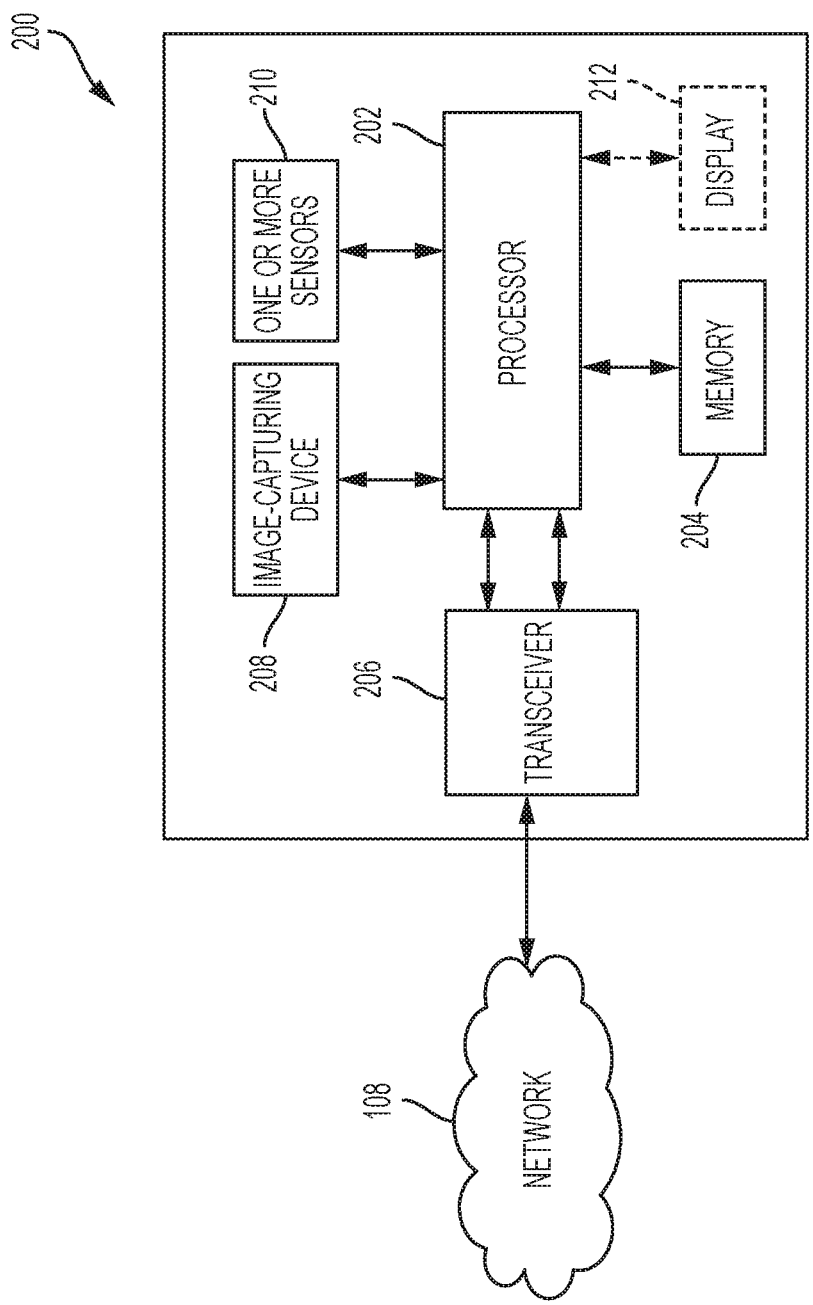
FIG. 2 is a block diagram that illustrates a system for predicting health condition of a patient, in accordance with at least one embodiment.

FIG. 2 is a block diagram that illustrates a system 200 for predicting the health condition of a patient, in accordance with at least one embodiment. The system 200 may comprise one or more processors, such as a processor 202, one or more memories, such as a memory 204, one or more transceivers, such as a transceiver 206, and one or more image capturing devices, such as an image-capturing device 208. The system 200 may further comprise one or more sensors 210, and a display 212.

The system 200 may correspond to the user-computing device 102 or the application server 106 without departing from the scope of the disclosure. For the purpose of the ongoing description, the system 200 has been considered as the application server 106.

The processor 202 may be configured to execute a set of instructions stored in the memory 204 to perform one or more operations. The processor 202 may be coupled to the memory 204, the transceiver 206, the image-capturing device 208, the one or more sensors 210, and the display 212. The processor 202 may be implemented based on a number of processor technologies known in the art. Examples of the processor 202 include, but are not limited to, an X86-based processor, a Reduced Instruction Set Computing (RISC) processor, an Application-Specific Integrated Circuit (ASIC) processor, a Complex Instruction Set Computing (CISC) processor, and/or other control circuits.

In an embodiment, the processor 202 may extract the set of medical records of the plurality of patients from a memory device, such as the database server 104. In an embodiment, the processor 202 may send a query through the output terminal to the database server 104 to extract the set of medical records of the plurality of patients. For example, based on an International Classification of Diseases (ICD) code used in the query, relevant records related to the health condition, may be extracted. In an embodiment, the transceiver 206 may receive the set of medical records of the plurality of patients through an input terminal. The set of medical records may be historical medical records of the plurality of patients that may be stored in the memory 204. In an embodiment, the processor 202 may segregate the set of medical records of the plurality of patients into two classes, a first set of medical records associated with the first class of patients (minority class) and a second set of medical records associated with the second class of patients (the majority class). The segregation of the set of medical records of the plurality of patients may be based on at least the heath condition (or medical complications) developed by the plurality of patients when they were under medical observation in the hospital. Due to the rarity of the health condition, the total number of patients included in the first class of patients may be lesser than the total number of patients in the second class of patients. Accordingly, the first set of medical records associated with the first class of patients and the second set of medical records associated with the second class of patients may represent imbalanced datasets.

In an embodiment, the processor 202 may extract data points from the first set of medical records associated with the first class of patients and the second set of medical records associated with the second class of patients. In an embodiment, the processor 202 may separately cluster data points associated with the first class of patients and the second class of patients. The processor 202 may determine a similarity value of each of the clustered data points with respect to a pre-selected subset of data points that represents landmark points. The similarity value may be determined by use of a parameterized similarity measure.

In an embodiment, the processor 202 may train one or more classifiers using the determined similarity value of each data point. The one or more classifiers may be adapted to learn one or more parameters of the parameterized similarity measure during the training. Such learning of the one or more parameters of the parameterized similarity measure during the training may improve classification performance for such imbalanced datasets. The training of the one or more classifiers will be explained in conjunction with FIG. 3A. After training the one or more classifiers, the processor 202 utilizes the trained one or more classifiers to determine/predict the health condition of a patient in advance when the patient may be under medical observation in a hospital. The determination/prediction may be based on one or more medical records of the patient. An example of such prediction will be explained later, in conjunction with FIG. 4B. The predicted occurrence of the health condition of the patient may be rendered on the display 212, via the user interface.

In an alternative embodiment, the functionalities of the processor 202, as described above, may be performed by one or more specialized processing units, such as a class determination unit, a data point extraction unit, a data point clustering unit, a landmark point selection unit, a similarity value determination unit, a training unit, a classification unit, a prediction unit, and an alert generation unit. In an embodiment, the one or more specialized processing units may be implemented as a separate processor or circuitry in the system 200. In an embodiment, the one or more specialized processing units and the processor 202 may be implemented as an integrated processor or a cluster of processors that perform the functions of the one or more specialized processing units and the processor 202, collectively. In an embodiment, the one or more specialized processing units may be implemented as a set of instructions stored in the memory 204, which upon execution by the processor 202 may perform the functions of the system 200. Such an implementation of the system 200 in the application server 106 has been described in detail, in accordance with an exemplary scenario, in FIGS. 4A and 4B. The memory 204 may be configured to store one or more machine codes, and/or a set of instructions having at least one code section executable by the processor 202. The memory 204 may store one or more sets of instructions or metadata associated with one or more patients (such as the new patient). Some of the commonly known memory implementations include, but are not limited to, a random access memory (RAM), a read-only memory (ROM), a hard disk drive (HDD), a secure digital (SD) card, and CPU cache. It will be apparent to a person having ordinary skill in the art that the set of instructions stored in the memory 204 enables the hardware of the system 200 to perform the predetermined operation.

The transceiver 206 may be configured to communicate with the one or more devices, such as the user-computing device 102, and/or one or more servers, such as the database server 104 over the network 108. The transceiver 206 may be configured to transmit or receive the set of medical records, the clinical investigation data, and/or the sensor-based patient monitoring data to/from various components of the system environment 100. In an embodiment, the transceiver 206 is coupled to the input terminal and the output terminal through which the transceiver 206 may receive or transmit data/messages/instructions associated with the one or more patients (such as new patients). In an embodiment, the input terminal and the output terminal may be realized through, but not limited to, an antenna, an Ethernet port, an USB port, or any other port that can be configured to receive and transmit data. The transceiver 206 may receive and transmit data/messages in accordance with various communication protocols such as, TCP/IP, UDP, and 2G, 3G, or 4G communication protocols through the input terminal and the output terminal, respectively.

The image-capturing device 208 is a device that optically scans images, printed text, handwriting, or an object, and converts it to a digital image. In an embodiment, the image-capturing device 208 may correspond to a scanner or a camera that may be utilized to scan the one or more documents (e.g., one or more nursing notes or investigative reports, etc.). In another embodiment, the image-capturing device 208 may be realized using one or more MFDs, such as the MFD 110. Though, the image-capturing device 208 is implemented within the application server 106 in FIG. 2, a person skilled in the art will appreciate the image-capturing device 208 to be depicted as independent from the application server 106 without departing from the scope of the disclosure. In an embodiment, the image-capturing device 208 may further include a CMOS sensor or a CCD sensor that may be used to capture the image of the one or more documents. In further embodiment, the image-capturing device 208 may utilize raster scanning techniques to capture the image of the one or more documents.

The one or more sensors 210 correspond to sensing devices that detect events or changes in quantities and provide a corresponding output, generally as an electrical or optical signal. In an embodiment, the one or more sensors 210 may correspond to a bio-sensor, which is configured to measure the one or more physiological parameters of the patient. In an embodiment, the one or more sensors 210 may be inbuilt within the system 200. Alternatively, the one or more sensors 210 may be separate sensing device(s), which may be communicatively or otherwise coupled to the system 200.

The display 212 may be configured to render one or more user interfaces (UIs) or application interfaces. The display 212 may be configured to render the predicted occurrence of the health condition of the patient, via at least one of the one or more UIs. The display 212 may be realized through several known technologies, such as liquid crystal display (LCD), light emitting diode (LED) based display, organic LED display technology, retina display technology, and/or the like.

Figure 3A:
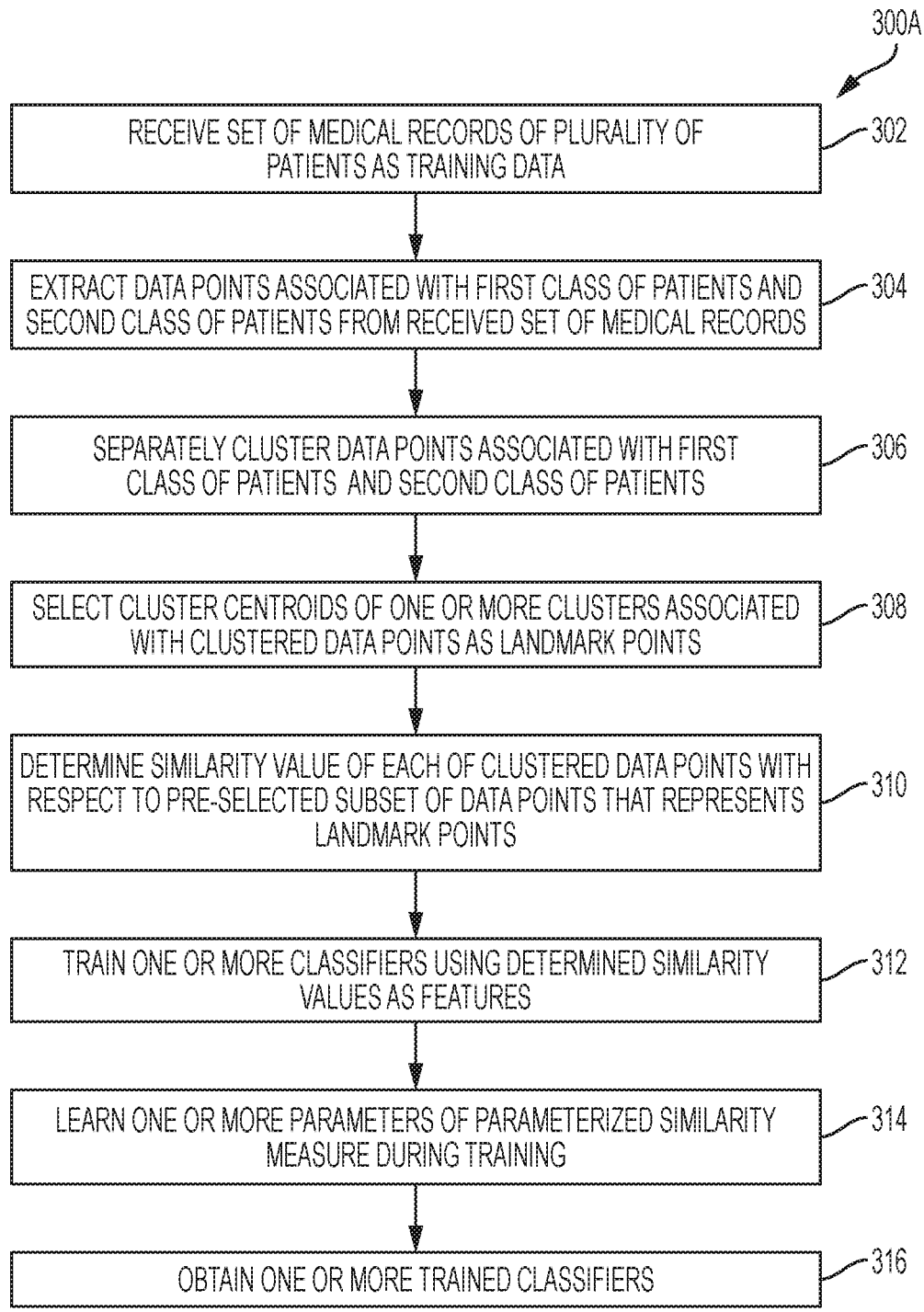
FIG. 3A is a flowchart that illustrates a method of training of one or more classifiers, in accordance with at least one embodiment.

FIG. 3A is a flowchart that illustrates a method of training of one or more classifiers, in accordance with at least one embodiment. FIG. 3A is a flowchart 300A described in conjunction with FIG. 1 and FIG. 2. The method starts at step 302.

At step 302, the set of medical records of the plurality of patients may be received. In an embodiment, the processor 202 may be configured to receive the set of medical records of the plurality of patients from one or more data sources. The set of medical records, thus received, may be utilized as training data. In an embodiment, the processor 202 may transmit a query to the database server 104 for retrieval of the set of medical records of the plurality of patients from the database server 104 over the network 108. In an embodiment, the query may be transmitted using the transceiver 206. In an embodiment, the query may include a standard code, such as International Classification of Diseases (ICD) code, to retrieve the set of medical records related to the health condition of the plurality of patients. In response to the transmitted query, the transceiver 206 may receive the set of medical records of the plurality of patients from the database server 104.

In an embodiment, the processor 202 may retrieve the set of medical records directly from various clinical data sources over the network 108. The clinical data sources may include, but are not limited to, databases of various medical organizations that may provide a rightful authentication to access the information pertaining to the plurality of patients or publicly available databases, such as MIMIC II®.

In an embodiment, the processor 202 may segregate the set of medical records of the plurality of patients into at least two classes, the first set of medical records and the second set of medical records. The first set of medical records may be associated with the first class of patients (minority class) and the second set of medical records may be associated with the second class of patients (the majority class), as discussed above. For example, the first set of medical records may comprise historical medical records of the first class of patients who was diagnosed with the heath condition, while the first class of patients was in the critical care unit (under medical observations). The second set of medical records may comprise historical medical records of the second class of patients who were not diagnosed with the heath condition, while the second class of patients were in critical care unit (under medical observations). For example, there are 800 patients associated with postoperative respiratory failure, of whom 120 were diagnosed with postoperative complications, such as acute respiratory failure (ARF), when they were under medical observation. In such a scenario, the medical records of the 120 patients are included in the first set of medical records (minority class), while the remaining medical records of the 680 patients are included in the second set of medical records (majority class).

At step 304, the data points, associated with both of the first class of patients and the second class of patients, may be extracted from the received set of medical records. In an embodiment, the processor 202 may be configured to extract the data points associated with the first class of patients and the second class of patients from the received set of medical records. The set of medical records of the plurality of patients may comprise text-based nursing notes and/or investigative reports associated with the plurality of patients. Such nursing notes and/or investigative reports may be valuable sources of information that indicate the health condition of the patients. For example, healthcare professionals, such as nurses, usually make such notes either periodically or based on events. Periodic notes may be prepared based on fixed time intervals, such as every four-five hours. Event-based notes may be prepared based on emergency events, such as a sudden drop in heart rate. Such nursing notes include objective as well as subjective evaluations of how a patient may be responding to medicines, a general well-being, and/or how the patient is feeling. Thus, such nursing notes and/or investigative reports may be valuable sources of text-based information. Although, such nursing notes and/or investigative reports are usually considered as unstructured, however, it is observed that data in such nursing notes and/or investigative reports may not be completely unstructured but may be structured into various headings, such as "CARDIO," "PULM," and "NEURO," etc.

After the segregation, the processor 202 may extract the one or more headings from the first set of medical records associated with the first class of patients (minority class) and the second set of medical records associated with the second class of patients (the majority class). For example, one or more words (related to medical science) from the phrases documented under each of the extracted one or more headings may be parsed using the one or more pre-defined rules/instructions stored in the memory 204. For example, if a word in the beginning of a sentence is followed by a colon, it may be considered heading. In an embodiment, the processor 202 may identify symbols (such as ":", paragraph spacing, the sentence before a paragraph begins, etc.) to identify the one or more headings. In an embodiment, the one or more headings may correspond to one or more medical specialties, such as neurology, cardiology, general medicine, pathology, oncology, urology, etc.

In certain scenarios, the nursing notes may not clearly indicate the headings. Further, the one or more healthcare professionals (e.g., doctors, nurses, and medical attenders) may have different ways of documenting the observations. In such a scenario, the processor 202 may be configured to refer to a medical dictionary to identify one or more synonymous terms in the one or more documents. For example, "CARDIO," "CV," and "CARD," all refer to the same heading.

Further, the processor 202 may be configured to identify the text written under such words or terms. Thereafter, the processor 202 may assign the same heading tag to each of the identified words. In an embodiment, the heading tag may be indicative of the heading under which the one or more words or phrases have been written. Thus, the data points associated with the first class of patients and the second class of patients may be extracted from the received set of medical records. In an embodiment, the processor 202 may be configured to extract similar or equivalent data points (or features) from other medical sources, such as the clinical investigation data and/or sensor-based patient monitoring data, which may correspond to historical data of the plurality of patients. In an embodiment, the clinical investigation data and/or sensor-based patient monitoring data may be a part of the received set of medical records.

In certain scenarios, the significance of the same word differs by heading. In such scenarios, features or headings of such words may be extracted separately and an importance value may be assigned to each word based on frequency of occurrence in the training data. In an exemplary instance, the text data for a single patient (until the diagnosis of ARF, for ARF patients) may be concatenated in accordance with a technique, text observation. One or more words within the same heading may be processed together for each text observation. Stemming, stop word removal, and punctuation removal may be performed to obtain a list of stem words under each heading, for each text observation. For example, the number of text observations may be denoted by, $n_w(C; H)$, where C is a class and w is a word that occurs under heading H. The importance of a word may be computed as, $I_w(H)=nw(A;H)-nw(B;H)$ for classes A and B. Thus, words that are more frequent in class A are positive and those in class B are negative and the importance value is an approximate measure of the discriminatory power of the word. For each heading H, words may be sorted with respect to corresponding importance values, $I_w(H)$. A pre-defined number, such as the top and bottom 5%, may be selected from both the most negative and most positive values, and the rest may be discarded. Within each heading, each of such words may form a feature and the number of occurrences of the word within a text observation may correspond to the feature value.

At step 306, the extracted data points associated with the first class of patients and the second class of patients may be separately clustered. In an embodiment, the processor 202 may separately cluster data points associated with the first class of patients (the minority class) and the second class of patients (the majority class). In an embodiment, various clustering algorithms known in the art, such as variants of K-Means and Density-Based Spatial Clustering of Applications with Noise (DBSCAN), may be used for clustering of the data points. Such clustering may be performed to provide diversification of landmark points, as discussed in the next step 308. In an embodiment, one or more parameters, such as a distribution parameter, may be set in each cluster.

At step 308, cluster centers of one or more clusters, such as the two clusters for the first class of patients and the second class, associated with clustered data points may be selected as landmark points. In an embodiment, the processor 202 may be configured to select a centroid of each cluster as a landmark point for the corresponding cluster. In an embodiment, K-Means, known in the art, may be used for the clustering, for which the number of landmark points for majority ($K=I_{maj}$) and minority ($K=I_{min}$) classes may be provided as input. The total number of landmark points, $I=I_{min}+I_{maj}$, may be selected from the range [P, 5p] using cross-validation on the training data, where p is the dimensionality of the dataset. A ratio ($I_{min}:I_{maj}$) may be maintained equal to an imbalance ratio. The imbalance ratio may be the ratio of the total number of data points in the majority class to that in the minority class in the training data.

At step 310, the similarity of each data point to a pre-selected subset of data points (which represents the landmark points) may be determined using a parameterized similarity function. In an embodiment, the processor 202 may be configured to determine the similarity between training points and landmark points using the parameterized similarity function. For example, a Gaussian kernel, a similarity function, such as the parameterized similarity function, may be used between the training points and the landmark points. In an embodiment, the similarity function between the PI p-dimensional data point, that is $x_i=[x_{i1}, x_{i2}, \ldots, x_{ip}]$ and $u^{th}$ landmark point, that is $L_U=[L_{u1}, L_{u2}, \ldots, L_{up}]$ is given by the following expression (1):

$$f_{iu} = e^{-\frac{1}{2}(x_i-L_u)^T \Sigma^{-1}(x_i-L_u)} \qquad (1)$$

where, $$\sum = \begin{bmatrix} \sigma_1^2 & \rho_{12}\sigma_1\sigma_2 & \cdots & \rho_{1p}\sigma_1\sigma_p \\ \rho_{21}\sigma_2\sigma_1 & \sigma_2^2 & \cdots & \rho_{2p}\sigma_2\sigma_p \\ \vdots & \vdots & \cdots & \vdots \\ \rho_{p1}\sigma_p\sigma_1 & \rho_{p2}\sigma_p\sigma_2 & \cdots & \sigma_p^2 \end{bmatrix}$$

is the corresponding deviance matrix;

$\sigma_j$ is the standard deviation along the $j^{th}$ dimension when the deviance is measured from
 the landmark points; and $\rho_{qr}$ is the correlation coefficient between the $q^{th}$ and the $r^{th}$ feature where the deviance is measured from the landmark point.

In an embodiment, the application of the similarity function on the training data by use of the mathematical expression (1), may be viewed as a transformation of the original dataset ($X_{n\times p}$) into a transformed dataset ($F_{n\times l}$), where each dimension represents similarity with respect to a landmark point. Each point after the transformation may be denoted as $(f_{iu})$, where $i=1, n$ and $u=1, \ldots, l$. For $(X_{n \times p})$, n corresponds to the number of data points in the training data, each of dimension, p. In an embodiment, various other similarity (or distance) functions, such as Manhattan kernel and/or Sigmoid kernel, may be used to compute similarities.

At step 312, one or more classifiers may be trained using the determined similarity value of each data point to all the landmark points. In an embodiment, the processor 202 may be configured to train the one or more classifiers using the determined similarity value of each data point to all the landmark points, where similarities are used as features. The one or more classifiers may be implemented using one or more machine learning algorithms, such as SVM, known in the art.

At step 314, one or more parameters of the parameterized similarity measure may be learned during the training. The one or more classifiers may be adapted to learn the one or more parameters of the parameterized similarity measure during the training. Instead of using a fixed similarity function, learning the parameters of the similarity function during training may improve classification performance for imbalanced datasets. In an embodiment, logistic regression may be adapted and a gradient descent based approach may be used, which simultaneously learns the similarity function parameter, $\Sigma$, as well as the logistic regression parameter, $\vartheta$.

For example, a logistic function, denoted by h, may be given by following mathematical expression (2):

$$h(f_\Sigma, \vartheta) = \text{sigmoid}(\theta_0 + \theta_1 f_1 + \ldots \theta_l f_l) \quad (2)$$

where,
$\vartheta = (\theta_0, \theta_1, \ldots, \theta_l)$;
$\theta_0$ is the bias term;
$\theta_u$ is the corresponding regression coefficient for the $u^{th}$ similarity value $f_u$; and
$f_\Sigma = [f_1, \ldots, f_l]$, is parameterized by $\Sigma$.

In an embodiment, to estimate the parameters, $\Sigma$ and $\vartheta$, the cost function may be minimized (the total misclassification error), as given by the following mathematical expression (3):

$$J(\vartheta, \Sigma) = -\frac{1}{n} \sum_{i=1}^{n} [y_i \log(h(f_\Sigma, \vartheta)) + (1-y_i) \log(1 - h(f_\Sigma, \vartheta))] \quad (3)$$

where,
$y_i$ is the class label corresponding to the $i^{th}$ observation $x_i$ ($i=1, 2, \ldots, n$) based on values "0" or "1."

Optimization may be done using the gradient descent. Learning $l+1$ logistic regression coefficients, $\vartheta$ and $p^2$, in the parameter, $\Sigma$, may be computationally expensive. Therefore, the correlation, $\rho$, may be estimated only once in the beginning and, the correlation, $\sigma$, may be estimated iteratively. Thus, only parameter, $l+p+1$, may be learnt during the gradient descent. This approach of initializing the parameter, $\Sigma$, (based on the correlation of input data points with the landmark points) during gradient descent may be better than random initialization.

In an embodiment, the initialization and update rules for the gradient descent to generate an output related to estimation of the parameters, $\Sigma$ and $\vartheta$, may be described by way of an example and may not be considered as a limitation, as given below. For example, dataset for training may be "$X_{n \times p}$," number of landmark points may be "l," and termination criteria may be "$\epsilon$." To initialize, "l" number of landmark points, $(L_1, L_2, \ldots, L_l)$ may be selected using K-Means on minority and majority class data points separately. The followings variables, in accordance with the expressions (4A) to 4(F), may be set:

$$\mu_j = 1/l \sum_{u=1}^{n} L_{uj} \quad (4A)$$

$$\sigma_j^{(0)2} = 1/n \sum_{i=1}^{n} (x_{ij} - \mu_j)^2 \quad (4B)$$

$$\rho_{qr} = 1/n \sum_{i=1}^{n} (x_{iq} - \mu_q)^2 (x_{ir} - \mu_r)/\sigma_q^0 \sigma_r^0 \quad (4C)$$

$$\sum{}^{(0)} = \begin{bmatrix} \sigma_1^{(0)2} & \rho_{12}\sigma_1^{(0)}\sigma_2^{(0)} & \cdots & \rho_{1p}\sigma_1^{(0)}\sigma_P^{(0)} \\ \rho_{21}\sigma_2^{(0)}\sigma_1^{0} & \sigma_2^{(0)2} & \cdots & \rho_{2p}\sigma_2^{(0)}\sigma_P^{(0)} \\ \vdots & \vdots & \cdots & \vdots \\ \rho_{p1}\sigma_P^{(0)}\sigma_1^{(0)} & \rho_{p2}\sigma_P^{(0)}\sigma_2^{(0)} & \cdots & \sigma_P^{(2)2} \end{bmatrix}_{P \times P} \quad (4D)$$

$$\vartheta^0 = [\theta_0^{(0)}, \theta_1^{(0)}, \ldots, \theta_l^{(0)}] = \left[\frac{1}{l+1}, \ldots, \frac{1}{l+1}\right]_{1 \times (l+1)} \quad (4E)$$

$$f_{iu}^{(0)} = e^{-\frac{1}{2}(x_i - L_u)^T \Sigma^{(0)-1}(x_i - L_u)} \quad (4F)$$

taken from expression (1));

Now, for the first iteration, and subsequent iterations is {for the $(k+1)^{st}$ iteration}, where "k" is the number of iterations, the following steps may be iteratively repeated.

$$\theta_u^{(k+1)} = \theta_u^{(k)} - \alpha_\vartheta \times \partial J^{(k)}/\partial \theta_u \quad (4G)$$

$$\sigma_j^{(k+1)} = \sigma_j^{(k)} - \alpha_\sigma \partial J^{(k)}/\partial \sigma_j \quad (4H)$$

where $\alpha_\vartheta$ and $\alpha_\sigma$ correspond to learning rates.

$$\frac{\partial J^{(k)}}{\partial \theta_u} = -\frac{1}{n} \sum_{i=1}^{n} (y_i - h(f_i^{(k)}, \vartheta^k)) f_{iu}^{(k)} \quad (4I)$$

$$\frac{\partial J^{(k)}}{\partial \sigma_j} = -\frac{1}{2n} \sum_{i=1}^{n} (y_i - h(f_i^{(k)}, \vartheta^{(k)}))[\theta_1^{(k)} f_{i1}^{(k)}, \ldots, \theta_l^{(k)} f_{i1}^{(k)}] \Delta_{ij} \quad (4J)$$

where $$\Delta_{ij} = \begin{bmatrix} (x_i - L_1)^T & \ldots & D_j^{(k)} & \ldots & (x_i - L_1) \\ & & \vdots & & \\ (x_i - L_1)^T & \ldots & D_j^{(k)} & \ldots & (x_i - L_l) \end{bmatrix}_{l \times 1} \quad (4K)$$

$$D_j^{(k)} = -\sum{}^{(k)-1} \frac{\partial \sum{}^{(k)}}{\partial \sigma_j} \sum{}^{(k)-1} \quad (4L)$$

until $J(\vartheta^{(k)}, \Sigma^k) < \epsilon$, where "J" is the cost function, as discussed above.
Thus, $$J(\vartheta^{(k)}, \Sigma^k) = \\ -\frac{1}{n} \sum_{i=1}^{n} [y_i \log(h(f_i^{(k)}, \vartheta^{(k)})) + (1-y_i) \log(1 - h(f_i^{(k)}, \vartheta^{(k)}))] \quad (4M)$$

taken from the expression (3) for the $k^{th}$ iteration),
where the logistic regression function h, of the mathematical expression (2) may be given as:

$$h(f_i^{(k)}, \vartheta^{(k)}) = \text{sigmoid}(\theta_0^{(k)} + \theta_1^{(k)} f_{i1}^{(k)} + \cdots + \theta_l^{(k)} f_{il}^{(k)}); \quad (2A)$$

and $$f_{iu}^{(k)} = e^{-\frac{1}{2}(x_i - L_u)^T \Sigma^{(k)-1}(x_i - L_u)}, \quad (1A)$$

(taken from expression (1))

For the expressions (4A) to (4L), (2A), and (1A), the following notations are used: indices j, q, r=1, . . . , p over dimensions;

i=1, . . . . , n over observations;

u=1, . . . , l over landmark points and (k) (in superscript) denotes number of iterations k.

Thus, the correlation σ may be estimated iteratively, as discussed in this example above, where $f_\Sigma$ may be used to compute similarities as features and the logistic regression function h ($f_\Sigma$, $\vartheta$) may be used for classification by the one or more classifiers with a chosen threshold value t.

At step 316, the trained one or more classifiers may be obtained. In an embodiment, the trained one or more classifiers may be stored in the memory 204 for later use. Thus, using labeled historical data from the two classes, i.e., the first class of patients who develop the heath condition, such as ARF, during their ICU stay, and the second class of patients who do not develop such heath conditions, the one or more classifiers may be trained. Such trained one or more classifiers may distinguish between the two classes. The trained one or more classifiers may be used to predict the class label of a new patient based on their data. For instance, if the predicted label is first class of patients, the patient is considered to be at risk for the health condition, such as ARF.

Figure 3B:
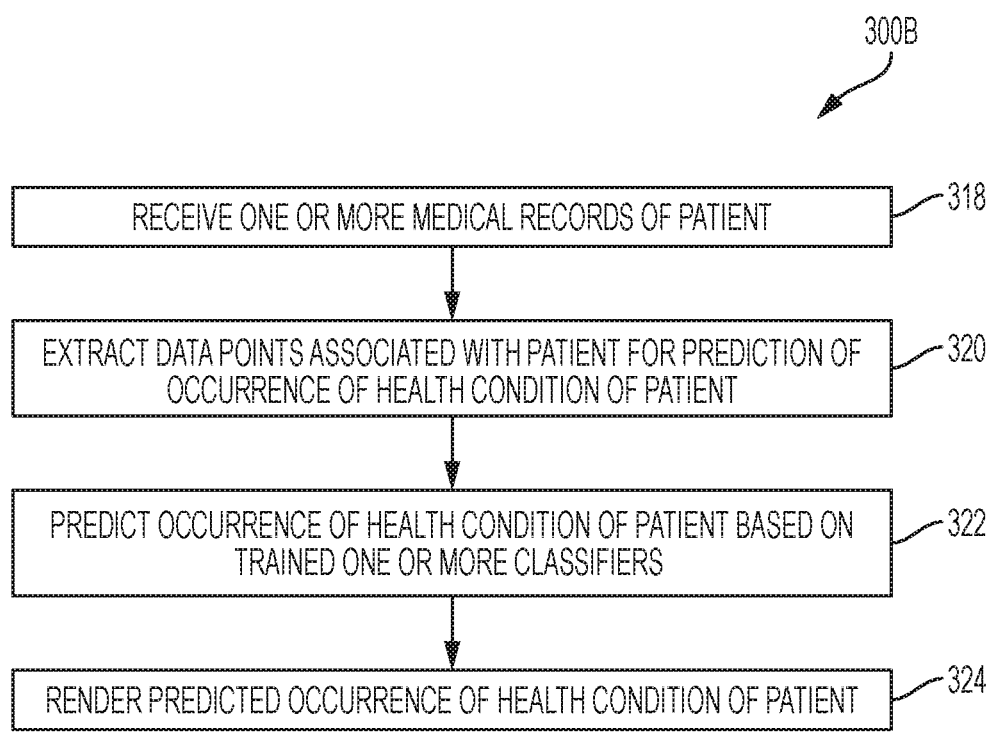
FIG. 3B is a flowchart that illustrates a method of predicting of a risk of occurrence of health condition of a new patient using trained one or more classifiers, in accordance with at least one embodiment.

FIG. 3B is a flowchart that illustrates a method of predicting of a risk of occurrence of health condition of a new patient using the trained one or more classifiers, in accordance with at least one embodiment. FIG. 3B is a flowchart 300B described in conjunction with FIG. 1, FIG. 2, and FIG. 3A. The method starts at step 318.

At step 318, one or more medical records of a patient, such as a new patient, may be received. The patient may be admitted to a hospital for treatment. In an embodiment, the processor 202 may receive the one or more medical records of the patient, who may be under medical observation, from the user-computing device 102 or the database server 104 over the network 108. The one or more medical records of the patient may comprise, but are not limited to, one or more clinical notes, such as nursing notes, investigative reports, etc., written by one or more healthcare professionals such as, but not limited to, a doctor, a nurse, or a medical attender. In an embodiment, the one or more medical records may be documented on a computing device, such as, but not limited to, a desktop computer, a laptop, a PDA, a mobile device, a smartphone, a tablet computer, and the like. However, the one or more medical records may be available either in the form of an electronic or handwritten record (such as one that is written with a pen and on a paper). In an embodiment, the handwritten medical records 112 may be scanned by utilizing the MFD 110 before transmitting them to the user-computing device 102. In case of the handwritten medical records (which may be stored in the database server 104), the processor 202 may utilize the image-capturing device 208 to scan the one or more handwritten medical records 112 associated with the patient (new patient).

In an embodiment, the processor 202 may further receive the one or more physiological parameters, such as, but not limited to, blood pressure, heart rate, respiratory rate, body temperature, and oxygen saturation of the patient. In an embodiment, the processor 202 may receive the one or more physiological parameters from the user-computing device 102 or the database server 104 over the network 108. In an embodiment, the processor 202 may utilize the one or more sensors 210 to measure the one or more physiological parameters of the patient. Thus, the one or more physiological parameters may be referred to as the real-time or near real-time sensor-based patient monitoring data. The one or more physiological parameters of the first patient may be continuously monitored through invasive or non-invasive methods. In an embodiment, the processor 202 may obtain the measured/observed/recorded data corresponding to the physiological parameters over a period of time associated with the patient.

At step 320, data points associated with the patient may be extracted from the received one or more medical records of the patient. The data points may be extracted for prediction of the occurrence of the health condition of the patient. In an embodiment, the processor 202 may be configured to extract the data points associated with the patient in a manner similar to that as described in step 304. The extracted data points may be provided to the trained one or more classifiers.

At step 322, an occurrence of the health condition of the patient may be predicted based on the trained one or more classifiers. The trained one or more classifiers may utilize the extracted data points from the received one or more medical records of the patient for the prediction. As discussed above, the one or more classifiers are trained using different classes of the historical medical records (the minority class and the majority class). For instance, if the patient is classified in the first class of patients, the patient is considered to be at risk for the health condition, such as ARF. Similarly, if the patient is classified in the second class of patients, the patient is considered not be at risk for the health condition. In an embodiment, the processor 202 may also predict morbidity, length of hospital stay, and risk of acquiring other complications by a patient under medical observation. After the logistic regression curve is fitted on the training data, a threshold, t (0<t<1), may be determined to classify test samples. For a test data point, "$x_i$," if h ($f_\Sigma$,$\vartheta$)>t, using the expression (2) or (2A), then a class "1" (such as the first class of patients) may be predicted, else class "0" may be predicted (such as the second class of patients). The threshold value, t, may be varied to obtain the complete receiver operating characteristic (ROC) of the disclosed method.

At step 324, the predicted occurrence of the health condition of the patient may be rendered on the display 212, via a user interface. A person skilled in the art will understand that the scope of the disclosure should not be limited to the prediction of the health condition of the patient who is under medical observation in the ICU. In an embodiment, the disclosed method and system may be utilized to predict the health condition of the patient who is undergoing treatment (not necessarily in the ICU) in the hospital. In another embodiment, the disclosed method and system may be utilized to predict the health condition of the patient who is undergoing the treatment at a second place such as, but not limited to, a medical camp, his/her house, or the like.

Figure 4A:
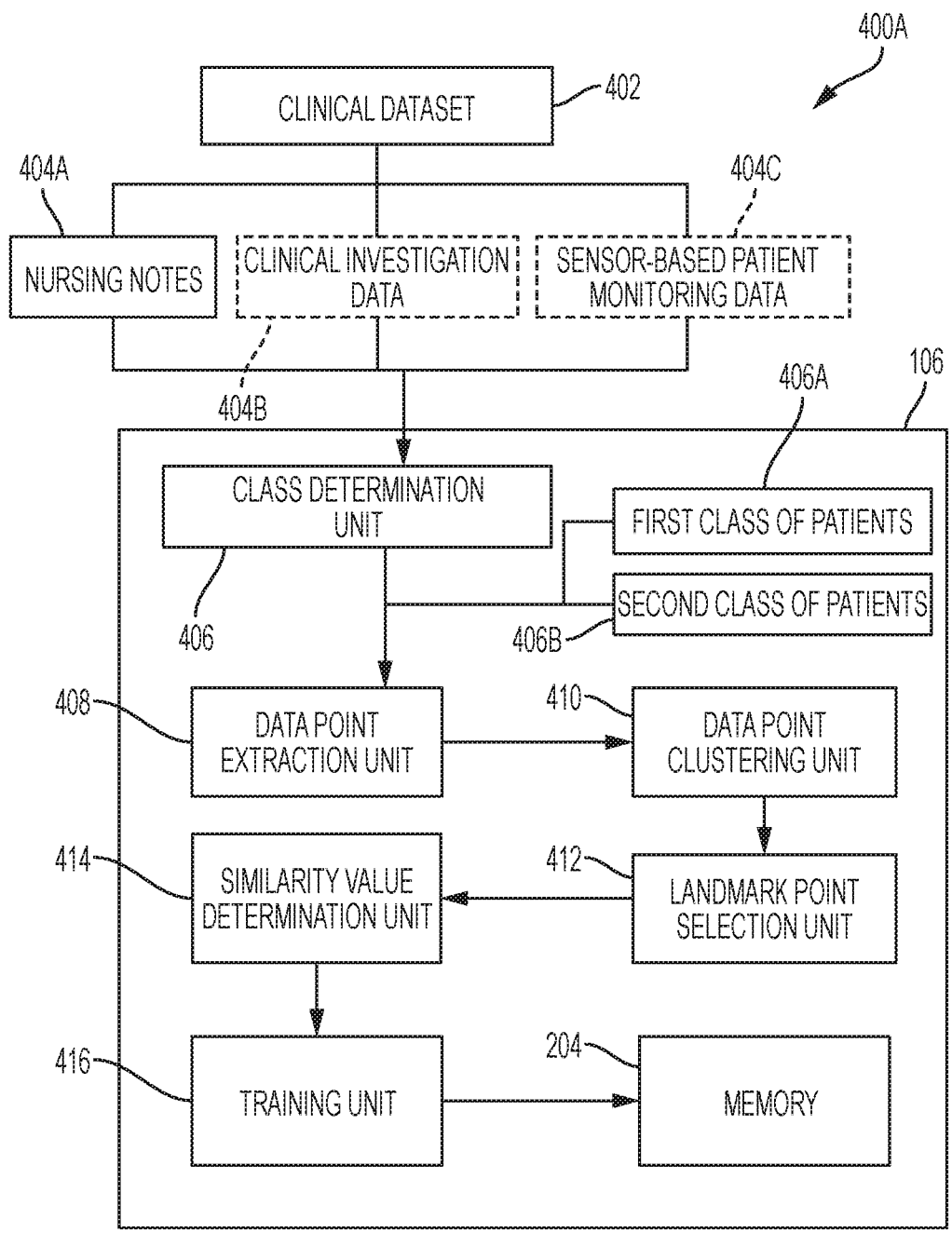
FIG. 4A is a block diagram that illustrates training of one or more classifiers using clinical datasets, in accordance with at least one embodiment.

FIG. 4A is a block diagram that illustrates training of one or more classifiers using clinical datasets, in accordance with at least one embodiment. The block diagram 400A is described in conjunction with FIG. 1, FIG. 2, FIG. 3A, and FIG. 3B. The block diagram 400A is explained by taking an example of the health condition as ARF.

With reference to FIG. 4A, there is further shown one or more specialized processing units, such as a class determination unit 406, a data point extraction unit 408, a data point clustering unit 410, a landmark point selection unit 412, a similarity value determination unit 414, and a training unit 416. In an embodiment, the one or more specialized processing units may be implemented as a separate processor or circuitry in the application server 106. In an embodiment, the one or more specialized processing units and the processor 202 may be implemented as an integrated processor or a cluster of processors that perform the functions of the one or more specialized processing units and the processor 202, collectively. In an embodiment, the one or more specialized processing units may be implemented as a set of instructions stored in the memory 204, which upon execution by the processor 202 may perform the functions of the application server 106.

With reference to FIG. 4A, there is shown training of one or more classifiers using a clinical dataset 402. The clinical dataset 402 may include nursing notes 404A, clinical investigation data 404B, and sensor-based patient monitoring data 404C of a plurality of patients. The clinical dataset 402 may be retrieved from the database server 104. Such nursing notes 404A include objective as well as subjective evaluations of how a patient may be responding to medicines, general well-being, and/or how the patient is feeling. Thus, the nursing notes 404A, clinical investigation data 404B, and/or sensor-based patient monitoring data 404C may be valuable sources of text-based information.

The class determination unit 406 may determine a first class of patients 406A and a second class of patients 406B from the plurality of patients based on the clinical dataset 402. The first class of patients 406A may be those patients who were diagnosed with post-operative complication, such as ARF. The second class of patients 406B may be those patients who were not diagnosed with ARF. Due to rarity of the post-operative complications of ARF, the number of second class of patients 406B may be much more than the first class of patients 406A. Thus, the clinical dataset 402 may be an imbalanced dataset.

In an embodiment, the data point extraction unit 408 may be configured to extract similar or equivalent data points (or features) from other medical sources, such as the clinical investigation data 404B and/or sensor-based patient monitoring data 404C. In an embodiment, nursing notes 404A, the clinical investigation data, 404B and/or sensor-based patient monitoring data 404C may be a part of the received set of medical records.

The data points associated with the first class of patients 406A and the second class of patients 406B may be extracted from the clinical dataset 402, by the data point extraction unit 408. The data points may be the training data. The data point clustering unit 410 separately clusters data points associated with the first class of patients 406A (the minority class) and the second class of patients 406B (the majority class). The landmark point selection unit 412 may be configured to select a centroid of each cluster as the landmark points. Thereafter, the similarity value determination unit 414 may be configured to determine a similarity between the training points (extracted data points) and the landmark points using the parameterized similarity function. Subsequently, the training unit 416 may be configured to train one or more classifiers using the determined similarity value of each data point. The determined similarity value of each data point (similarities) is used as features. $f_\Sigma$ may be used to compute similarities as features. The mathematical expressions (1), (1A), and (4D) (the deviance matrix) may be used for such computation. The one or more classifiers may be adapted to learn one or more parameters of the parameterized similarity measure during the training, which improves classification performance for the imbalanced dataset. Consequently, the trained one or more classifiers may be obtained.

Figure 4B:
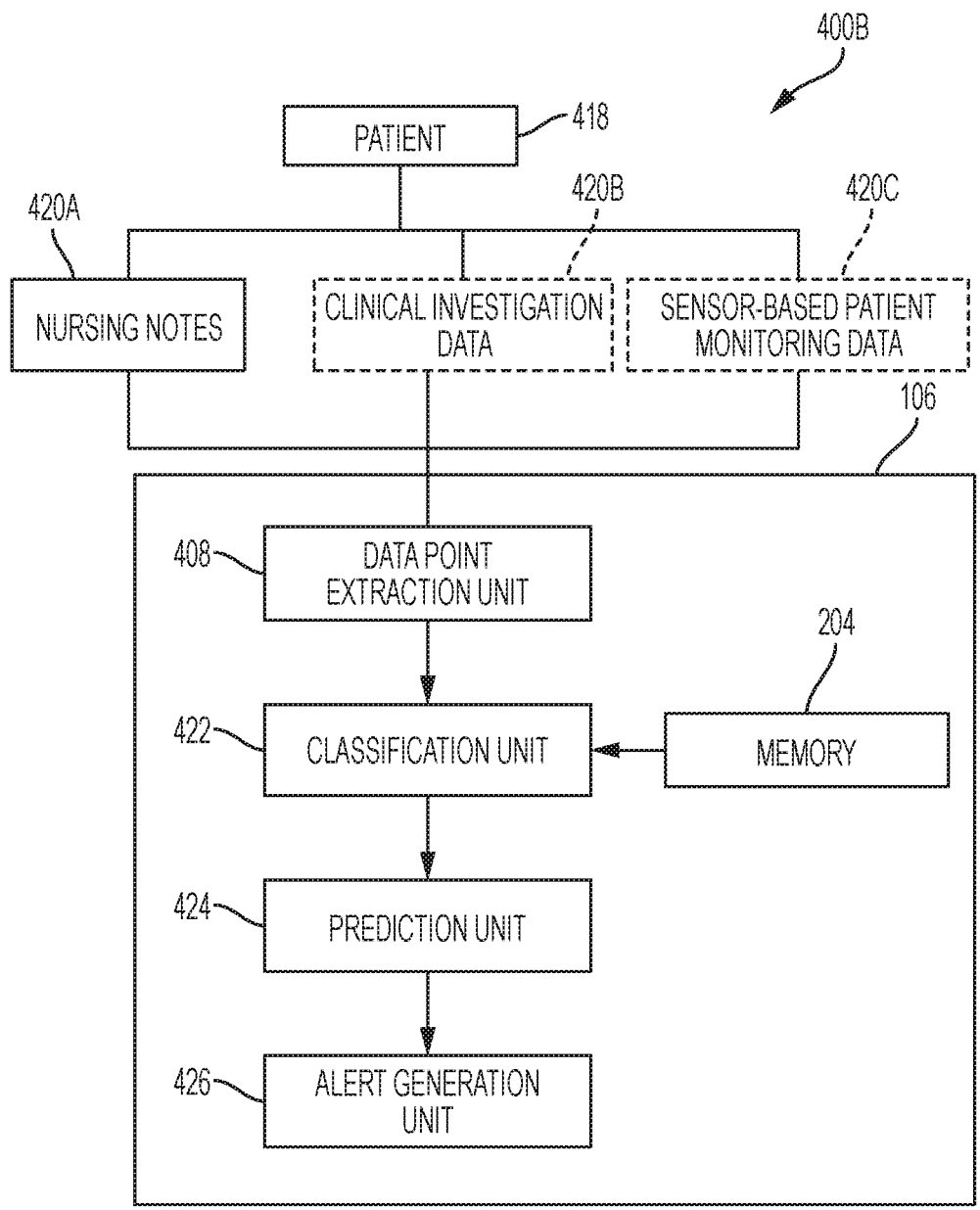
FIG. 4B is a block diagram that illustrates prediction of a risk of occurrence of health condition of a new patient using trained one or more classifiers, in accordance with at least one embodiment.

FIG. 4B is a block diagram that illustrates prediction of a risk of occurrence of health condition of a new patient using the trained one or more classifiers obtained from FIG. 4A, in accordance with at least one embodiment. The block diagram 400B is described in conjunction with FIG. 1, FIG. 2, FIG. 3A, FIG. 3B, and FIG. 4A. The block diagram 400A is explained by taking an example of the health condition as ARF.

With reference to FIG. 4B, there is shown a new patient, such as the patient 418, admitted to a hospital for treatment and who may be under medical observation. One or more medical records of the patient 418 may include the nursing notes 420A, clinical investigation data 420B, and the sensor-based patient monitoring data 420C. There is further shown one or more specialized processing units, such as the class determination unit 406, the data point extraction unit 408, a classification unit 422, a prediction unit 424, and an alert generation unit 426. In an embodiment, the one or more specialized processing units may be implemented as a separate processor or circuitry in the application server 106. In an embodiment, the one or more specialized processing units and the processor 202 may be implemented as an integrated processor or a cluster of processors that perform the functions of the one or more specialized processing units and the processor 202, collectively. In an embodiment, the one or more specialized processing units may be implemented as a set of instructions stored in the memory 204, which upon execution by the processor 202 may perform the functions of the application server 106.

The data point extraction unit 408 may be configured to extract the data points associated with the patient 420. The classification unit 422 may be configured to fit the logistic regression curve that corresponds to the extracted data points associated with the patient 420 on the training data, based on the one or more classifiers trained by the training unit 416. Based on the curve fitting, the classification unit 422 may be configured to classify the patient 418 into class "1" (such as the first class of patients 406A) or class "0" (such as the second class of patients 406B). For a test data point, "$x_i$," if h ($f_\Sigma$, $\vartheta$)>t, using the mathematical expression (2) or (2A), class "1" (such as the first class of patients) may be predicted, else class "0" may be predicted (such as the second class of patients).

Based on the classification of the patient 418, the prediction unit 424 may predict the risk of occurrence of ARF for the patient 418. The prediction unit 424 may be configured to predict whether the patient 418 is at a risk for the occurrence of ARF in advance, based on the trained one or more classifiers and the extracted data points. The alert generation unit 426 may generate an alert that may be sent to an electronic device associated with a doctor or a healthcare professional attending the patient 418. When the patient 418 is classified in the first class of patients 406A (i.e., the minority class), the patient 418 is considered to be at risk for ARF. Similarly, when the patient 418 is classified in the second class of patients 406B (i.e., the majority class), the patient 418 is considered not be at risk for ARF. Thus, adequate measures may be taken in advance to avoid or mitigate the predicted heath condition for the patient 418, such as ARF in this case.

Various embodiments of the disclosure lead to prediction of the health condition of a patient who is under medical observation. The disclosed method utilizes the one or more medical records of the patient such as the text sources of information (nursing notes, investigative reports, etc.) to predict the postoperative health condition of the patient. The disclosed method further utilizes the statistical features extracted from the one or more vital signs (blood pressure, heart rate, respiratory rate, etc.) to predict the health condition of the patient. The disclosed system is a real time clinical surveillance system that attempts to identify emerging complications (e.g., stroke, urinary tract infections, myocardial infarctions, etc.) for the patient under medical observation, so that a risk of complication/medical emergency can be identified and treated before the patient is discharged from the hospital. Further, the disclosed system may help in reducing penalties associated with re-admission of the patient, thereby economizing the operations of a medical care center.

The disclosed methods and systems, as illustrated in the ongoing description or any of its components, may be embodied in the form of a computer system. Typical examples of a computer system include a general-purpose computer, a programmed microprocessor, a micro-controller, a peripheral integrated circuit element, and other devices, or arrangements of devices that are capable of implementing the steps that constitute the method of the disclosure.

The computer system comprises a computer, an input device, a display unit and the Internet. The computer further comprises a microprocessor. The microprocessor is connected to a communication bus. The computer also includes a memory. The memory may be Random Access Memory (RAM) or Read Only Memory (ROM). The computer system further comprises a storage device, which may be a hard-disk drive or a removable storage drive, such as, a floppy-disk drive, optical-disk drive, and the like. The storage device may also be a means for loading computer programs or other instructions into the computer system. The computer system also includes a communication unit. The communication unit allows the computer to connect to other databases and the Internet through an input/output (I/O) interface, allowing the transfer as well as reception of data from other sources. The communication unit may include a modem, an Ethernet card, or other similar devices, which enable the computer system to connect to databases and networks, such as, LAN, MAN, WAN, and the Internet. The computer system facilitates input from a user through input devices accessible to the system through an I/O interface.

In order to process input data, the computer system executes a set of instructions that are stored in one or more storage elements. The storage elements may also hold data or other information, as desired. The storage element may be in the form of an information source or a physical memory element present in the processing machine.

The programmable or computer-readable instructions may include various commands that instruct the processing machine to perform specific tasks, such as steps that constitute the method of the disclosure. The systems and methods described can also be implemented using only software programming or using only hardware or by a varying combination of the two techniques. The disclosure is independent of the programming language and the operating system used in the computers. The instructions for the disclosure can be written in all programming languages including, but not limited to, "C," "C++," "Visual C++," Java, and "Visual Basic." Further, the software may be in the form of a collection of separate programs, a program module containing a larger program or a portion of a program module, as discussed in the ongoing description. The software may also include modular programming in the form of object-oriented programming. The processing of input data by the processing machine may be in response to user commands, the results of previous processing, or from a request made by another processing machine. The disclosure can also be implemented in various operating systems and platforms including, but not limited to, "Unix," "DOS," "Android," "Symbian," and "Linux."

The programmable instructions can be stored and transmitted on a computer-readable medium. The disclosure can also be embodied in a computer program product comprising a computer-readable medium, or with any product capable of implementing the above methods and systems, or the numerous possible variations thereof.

Various embodiments of the methods and systems for predicting a health condition of a patient have been disclosed. However, it should be apparent to those skilled in the art that modifications in addition to those described, are possible without departing from the inventive concepts herein. The embodiments, therefore, are not restrictive, except in the spirit of the disclosure. Moreover, in interpreting the disclosure, all terms should be understood in the broadest possible manner consistent with the context. In particular, the terms "comprises" and "comprising" should be interpreted as referring to elements, components, or steps, in a non-exclusive manner, indicating that the referenced elements, components, or steps may be present, or utilized, or combined with other elements, components, or steps that are not expressly referenced.

A person having ordinary skills in the art will appreciate that the system, modules, and sub-modules have been illustrated and explained to serve as examples and should not be considered limiting in any manner. It will be further appreciated that the variants of the above disclosed system elements, or modules and other features and functions, or alternatives thereof, may be combined to create other different systems or applications.

Those skilled in the art will appreciate that any of the aforementioned steps and/or system modules may be suitably replaced, reordered, or removed, and additional steps and/or system modules may be inserted, depending on the needs of a particular application. In addition, the systems of the aforementioned embodiments may be implemented using a wide variety of suitable processes and system modules and is not limited to any particular computer hardware, software, middleware, firmware, microcode, or the like.

The claims can encompass embodiments for hardware, software, or a combination thereof. It will be appreciated that variants of the above disclosed, and other features and functions or alternatives thereof, may be combined into many other different systems or applications. Presently unforeseen or unanticipated alternatives, modifications, variations, or improvements therein may be subsequently made by those skilled in the art, which are also intended to be encompassed by the following claims.

What is claimed is:

1. A system for training a computing device for predicting a health condition of a patient, the system comprising:

one or more transceivers in the computing device configured to retrieve a set of medical records of a plurality of patients from a memory device, wherein the set of medical records corresponds to a first class of patients diagnosed with the health condition and a second class of patients not diagnosed with the health condition;

one or more processors in the computing device configured to:
separately cluster data points associated with the first class of patients and the second class of patients and select landmark points;
train a classifier that uses a logistic regression curve to classify input data,
wherein the logistic regression curve has a regression parameter and similarity terms representing similarity with respect to the landmark points, the similarity terms each corresponding to a gaussian kernel having an input variable and a kernel parameter,
wherein training the classifier includes simultaneously learning a value for the kernel parameter together with learning a value for the regression parameter in a same training operation comprising minimizing a same cost function based on the clustered data points;
wherein the trained classifier is configured to:
extract data associated with the patient from one or more medical records of the patient;
evaluate the logistic regression curve with the extracted data as the input data;
classify the patient into the first class or second class based on a result of evaluating the logistic regression curve;
predict an occurrence of the health condition of the patient based on the classification; and
generate a representation of the predicted occurrence of the health condition of the patient for displaying via a user interface.

2. The system of claim 1, wherein each of the set of medical records of the plurality of patients comprises at least one of: a text-based nursing note and an investigative report.

3. The system of claim 1, wherein the one or more processors are further configured to extract the data points associated with the first class of patients and the second class of patients from one or more of: the retrieved set of medical records, clinical investigation data, and/or sensor-based patient monitoring data that corresponds to one or more physiological parameters of the plurality of patients.

4. The system of claim 3, wherein the extracted data points associated with the first class of patients corresponds to an underrepresented class or a minority class, and wherein the extracted data points associated with the second class of patients corresponds to an overrepresented class or a majority class.

5. The system of claim 1, wherein the one or more processors are configured to select cluster centers of one or more clusters associated with the clustered data points as the landmark points.

6. The system of claim 1, wherein the one or more processors are configured to update the gaussian kernel based on the learned value of the kernel parameter.

7. The system of claim 1, wherein the one or more medical records of the patient, corresponding to a documentation of a medical observation of the patient by a medical attender, are retrieved by the one or more transceivers to extract data points associated with the patient for the prediction of the occurrence of the health condition of the patient.

8. The system of claim 7, further comprising one or more sensors configured to measure one or more physiological parameters associated with the patient, wherein the one or more physiological parameters comprise one or more of: blood pressure, heart rate, respiratory rate, body temperature, and oxygen saturation.

9. The system of claim 7, wherein the occurrence of the health condition of the patient is predicted when the result of evaluating the logistic regression curve based on the extracted data is greater than a pre-determined threshold.

10. The system of claim 9, wherein the generated representation of the prediction of the occurrence of the health condition of the patient indicates a risk of the occurrence of the health condition of the patient in a real-time or near real-time.

11. A method for training a computing device for predicting a health condition of a patient, the method comprising:
retrieving, by one or more transceivers in the computing device, a set of medical records of a plurality of patients from a memory device, wherein the set of medical records corresponds to a first class of patients diagnosed with the health condition and a second class of patients not diagnosed with the health condition;
separately clustering, by one or more processors in the computing device, data points associated with a first class of patients and a second class of patients and selecting landmark points;
training a classifier that uses a logistic regression curve to classify input data,
wherein the logistic regression curve has a regression parameter and similarity terms representing similarity with respect to the landmark points, the similarity terms each corresponding to a gaussian kernel having an input variable and a kernel parameter,
wherein training the classifier includes simultaneously learning a value for the kernel parameter together with learning a value for the regression parameter in a same training operation comprising minimizing a same cost function based on the clustered data points;
extracting data associated with the patient from one or more medical records of the patient;
evaluating the logistic regression curve with the extracted data as the input data;
classifying the patient into the first class or second class based on a result of evaluating the logistic regression curve;
predicting, by the trained classifier, an occurrence of the health condition of the patient based on the classification; and
generating, by the one or more processors, a representation of the predicted occurrence of the health condition of the patient for displaying via a user interface.

12. The method of claim 11, wherein each of the set of medical records of the plurality of patients comprises at least one of: a text-based nursing note and an investigative report.

13. The method of claim 11 further comprising extracting, by the one or more processors, the data points associated with the first class of patients and the second class of patients from one or more of: the retrieved set of medical records, clinical investigation data, and/or sensor-based patient monitoring data that corresponds to one or more physiological parameters of the plurality of patients.

14. The method of claim 13, wherein the extracted data points associated with the first class of patients corresponds to an underrepresented class or a minority class and wherein the extracted data points associated with the second class of patients corresponds to an overrepresented class or a majority class.

15. The method of claim 11 further comprising selecting, by the one or more processors, cluster centers of one or more clusters associated with the clustered data points as the landmark points.

16. The method of claim 11 further comprising updating, by the one or more processors, the gaussian kernel based on the learned value of the kernel parameter.

17. The method of claim 11, wherein the one or more medical records of the patient, corresponding to a documentation of a medical observation of the patient by a medical attender, are received by the one or more transceivers to extract data points associated with the patient for the prediction of the occurrence of the health condition of the patient.

18. The method of claim 17, wherein the occurrence of the health condition of the patient is predicted responsive to the result of evaluating the logistic regression curve based on the extracted data points associated with the patient being greater than a pre-determined threshold.

19. The method of claim 11, wherein the generated representation of the prediction of the occurrence of the health condition of the patient indicates a risk of the occurrence of the health condition of the patient in a real-time or near real-time.

20. A computer program product for use with a computer, the computer program product comprising a non-transitory computer readable medium, wherein the non-transitory computer readable medium stores a computer program code for training a computing device for predicting a health condition of a patient, wherein the computer program code is executable by one or more processors to:

retrieve, by use of one or more transceivers in the computing device, a set of medical records of a plurality of patients from a memory device, wherein the set of medical records corresponds to a first class of patients diagnosed with the health condition and a second class of patients not diagnosed with the health condition; and separately cluster data points associated with the first class of patients and the second class of patients and select landmark points;

train a classifier that uses a logistic regression curve to classify input data,
 wherein the logistic regression curve has a regression parameter and similarity terms representing similarity with respect to the landmark points, the similarity terms each corresponding to a parametrized similarity function having an input variable and a similarity parameter,
 wherein training the classifier includes simultaneously learning a value for the similarity parameter together with learning a value for the regression parameter in a same training operation comprising minimizing a same cost function based on the clustered data points;

extract data associated with the patient from one or more medical records of the patient;

evaluate the logistic regression curve with the extracted data as the input data;

classify the patient into the first class or second class based on a result of evaluating the logistic regression curve;

predict, by the trained classifier, an occurrence of the health condition of the patient based on the classification; and generate a representation of the predicted occurrence of the health condition of the patient for displaying via a user interface.

* * * * *